US011880061B2

United States Patent
Zalevsky et al.

(10) Patent No.: US 11,880,061 B2
(45) Date of Patent: Jan. 23, 2024

(54) OPTICAL FIBER FROM A SINGLE POLYMER

(71) Applicant: ZSquare Ltd., Petah Tikva (IL)

(72) Inventors: Zeev Zalevsky, Rosh Ha'ayin (IL);
Asaf Shahmoon, Petah Tikva (IL);
Amihai Meiri, Ramat Hasharon (IL);
Oran Herman, Givat Shmuel (IL)

(73) Assignee: ZSQUARE LTD., Petah Tikva (IL)

( * ) Notice: Subject to any disclaimer, the term of this patent is extended or adjusted under 35 U.S.C. 154(b) by 0 days.

(21) Appl. No.: 17/503,266

(22) Filed: Oct. 16, 2021

(65) Prior Publication Data

US 2023/0117022 A1   Apr. 20, 2023

(51) Int. Cl.
*G02B 6/02* (2006.01)
*B29C 35/08* (2006.01)
*B29C 59/16* (2006.01)

(52) U.S. Cl.
CPC ...... *G02B 6/02033* (2013.01); *B29C 35/0805* (2013.01); *B29C 59/16* (2013.01); *G02B 6/02042* (2013.01); *B29C 2035/0827* (2013.01)

(58) Field of Classification Search
CPC ........ B29C 35/0805; B29C 2035/0827; B29C 59/16; B29C 59/165; G02B 6/02033; G02B 6/02042
USPC ................................. 264/1.27, 1.24
See application file for complete search history.

(56) References Cited

U.S. PATENT DOCUMENTS

| 6,527,985 B1 | 3/2003 | Franck et al. |
| 7,294,454 B1 | 11/2007 | Said et al. |
| 2015/0315072 A1* | 11/2015 | Saito ................. G02B 6/02033 427/513 |

FOREIGN PATENT DOCUMENTS

| DE | 102019132569 B3 * | 2/2021 |
| EP | 0472384 A2 * | 2/1992 |
| JP | 2013224974 | 10/2013 |
| WO | WO2016/123719 | 8/2016 |

OTHER PUBLICATIONS

English translation of DE-102019132596-B3, Feb. 2021, Bartelt, H.*

* cited by examiner

*Primary Examiner* — Philip C Tucker
*Assistant Examiner* — Jimmy R Smith, Jr.
(74) *Attorney, Agent, or Firm* — PEARL COHEN ZEDEK LATZER BARATZ LLP

(57) ABSTRACT

A system for producing a multicore optical fiber includes a source of electromagnetic radiation in a spectral range that is suitable for inducing photopolymerization of a transparent polymer. An arrangement of one or more optical components is configured to concurrently focus the radiation that is emitted by the source on a plurality of elongated regions of the transparent polymer so as to photopolymerize the transparent polymer solely in the elongated regions to increase the index of refraction of the elongated regions such that in the optical fiber that is formed of the transparent polymer after the elongated regions are photopolymerized, each of the elongated regions functions as a core of the optical fiber and regions of the transparent polymer that surround the elongated regions function as a cladding of each of the cores.

7 Claims, 3 Drawing Sheets

OPTICAL FIBER FROM A SINGLE POLYMER

FIELD OF THE INVENTION

The present invention relates to endoscopes. More particularly, the present invention relates to optical fibers produced from a single polymer for incorporation, for example, in a multicore micro-endoscope.

BACKGROUND OF THE INVENTION

A micro-endoscope may be utilized to image microscopic structures, e.g., within the body of a living organism or an object. The micro-endoscope may include one or more optical fibers, one end of which may be inserted within a space that contains the structure that is to be imaged. The other end of each optical fiber may be connected to an optical device that enables viewing of imaged structure.

A multicore micro-endoscope typically includes a bundle of optical fiber cores that are embedded within a single shared cladding. The index of refraction of the core is configured to be sufficiently greater than the index of refraction of the cladding such that light that enters one end of the fiber is transmitted to the other end with minimal loss and with minimal crosstalk between fiber cores.

SUMMARY OF THE INVENTION

There is thus provided, in accordance with an embodiment of the invention, a system for producing a multicore optical fiber, the system including: a source of electromagnetic radiation in a spectral range that is suitable for inducing photopolymerization of a transparent polymer; and an arrangement of one or more optical components configured to concurrently focus the radiation that is emitted by the source on a plurality of elongated regions of the transparent polymer so as to photopolymerize the transparent polymer solely in the elongated regions to increase the index of refraction of the elongated regions such that in the optical fiber that is formed of the transparent polymer after the elongated regions are photopolymerized, each of the elongated regions functions as a core of the optical fiber and regions of the transparent polymer that surround the elongated regions function as a cladding of each of the cores.

Furthermore, in accordance with an embodiment of the invention, the spectral range includes ultraviolet radiation.

Furthermore, in accordance with an embodiment of the invention, the source includes an excimer laser.

Furthermore, in accordance with an embodiment of the invention, the excimer laser emits ultraviolet radiation in a spectral range from 100 nm to 400 nm.

Furthermore, in accordance with an embodiment of the invention, the optical components are arranged in a cylindrical configuration.

Furthermore, in accordance with an embodiment of the invention, the optical components include a linear cylindrical lens.

Furthermore, in accordance with an embodiment of the invention, the optical components include a laterally curved cylindrical lens.

Furthermore, in accordance with an embodiment of the invention, the optical components include a beam-shaping component.

There is further provided, in accordance with an embodiment of the invention, a multicore optical fiber including a transparent polymer whose index of refraction is increasable by photopolymerization by irradiation, the optical fiber including one or a plurality of cores that extend along the length of the fiber, each of the cores formed by photopolymerization of the transparent polymer, wherein each of the cores is surrounded by a cladding including regions of the transparent polymer that were not irradiated.

Furthermore, in accordance with an embodiment of the invention, the transparent polymer includes poly(methyl methacrylate) (PMMA).

Furthermore, in accordance with an embodiment of the invention, the irradiation includes electromagnetic radiation in the ultraviolet spectral range.

Furthermore, in accordance with an embodiment of the invention, each of the cores is formed by irradiation of a pre-form of the transparent polymer, the pre-form having been stretched to form the optical fiber.

Furthermore, in accordance with an embodiment of the invention, each of the cores is formed by irradiation of a fiber of the transparent polymer There is further provided, in accordance with an embodiment of the invention, a method for producing a multicore optical fiber, the method including: providing a transparent polymer whose index of refraction is increasable by irradiation that induces photopolymerization of the transparent polymer; providing a source of radiation that is capable of inducing photopolymerization in the transparent polymer; and directing the radiation by one or more optical components to a plurality of elongated regions within the transparent polymer to induce the photopolymerization of the transparent polymer within the plurality of elongated regions, each of the elongated regions surrounded by a region of the transparent polymer that was not photopolymerized, such that in an optical fiber that is formed of the transparent polymer after the photopolymerization, each of the elongated regions functions as a core of the optical fiber and the region that surround each of the elongated regions functions as a cladding of each of the cores.

Furthermore, in accordance with an embodiment of the invention, the transparent polymer is provided in the form of a pre-form of the transparent polymer.

Furthermore, in accordance with an embodiment of the invention, the method includes stretching the pre-form to dimensions of the optical fiber.

Furthermore, in accordance with an embodiment of the invention, the one or more optical components include a beam-shaping component to enable concurrent irradiation of a plurality of the cores.

Furthermore, in accordance with an embodiment of the invention, the transparent polymer is provided in the form of a fiber of the transparent polymer.

Furthermore, in accordance with an embodiment of the invention, the fiber of the transparent polymer is provided in the form of a spiral coil.

Furthermore, in accordance with an embodiment of the invention, directing the radiation includes successively directing the radiation to a plurality of the elongated regions in one part of the fiber, and mechanically moving the fiber, and directing the radiation to plurality of the elongated regions in another one part of the fiber.

BRIEF DESCRIPTION OF THE DRAWINGS

In order for the present invention to be better understood and for its practical applications to be appreciated, the following Figures are provided and referenced hereafter. It should be noted that the Figures are given as examples only FIG. 1 schematically illustrates a section of a multicore micro-endoscope, in accordance with some embodiments of the invention.

DETAILED DESCRIPTION OF THE INVENTION

Figure 1:
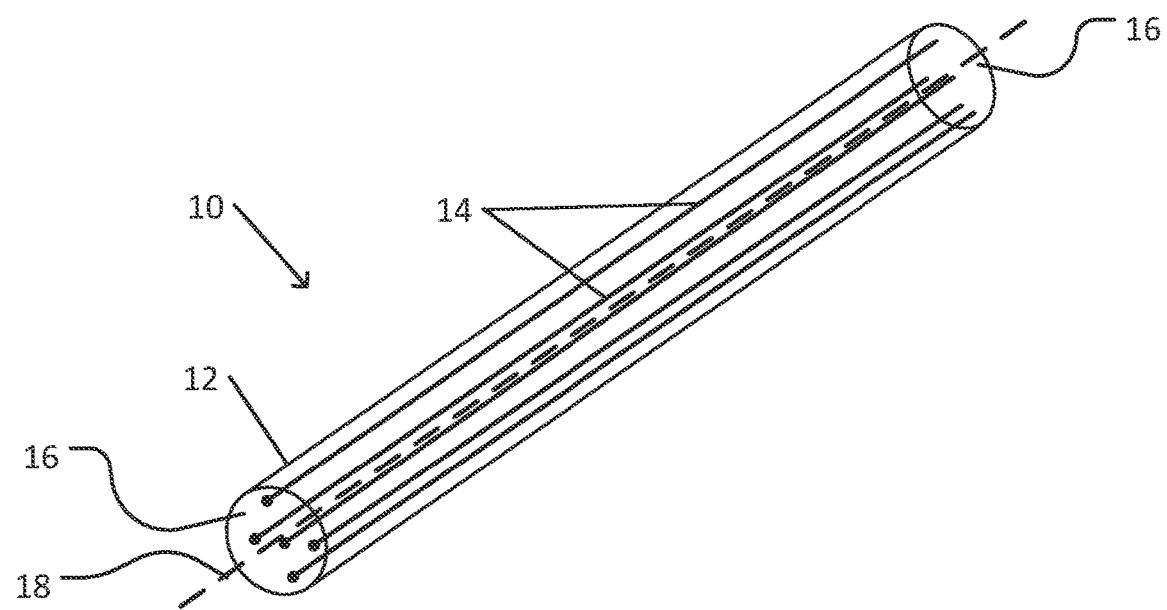

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

In accordance with some embodiments of the invention, a multicore micro-endoscope is formed by irradiating one or more elongated regions of a transparent polymer with radiation that is configured to induce photopolymerization solely in the elongated regions. The irradiation may result in an increase of the index of refraction of the elongated regions over the index of refraction of the remaining regions of the polymer that were not irradiated. Thus, each irradiated elongated region may function as a fiber optic core, while the regions of the polymer that were not irradiated function as cladding of the cores.

For example, the transparent polymer may include polymethyl methacrylate (PMMA) or another suitable thermoplastic material (e.g., as opposed to a thermoset material) whose index of refraction may be increased by a photopolymerization process while remaining plastic and flexible. Typically, the irradiation for the photopolymerization process is in the ultraviolet spectral range. For example, the source of the ultraviolet radiation may include an excimer laser or other source, e.g., that emits radiation in a spectral range with wavelengths between 100 nm and 400 nm, or another suitable spectral range.

For example, the contrast in index of refraction after the photopolymerization may be in the range of 0.01 to 0.04. Since photopolymerization typically depends nonlinearly on the intensity of the irradiation, the contrast between the indices of refraction in the photopolymerized and non-photopolymerized regions of the transparent polymer may be step-like, rather than gradual. This range of contrast may be sufficient for many applications of multicore micro-endoscopy.

In some cases, a fiber with a single core may be formed by irradiating a pre-form (an elongated block of the transparent polymer whose length is much less than the length of an optical fiber and whose lateral dimensions are much wider than those of the optical fiber), e.g., via a linear cylindrical focusing lens or other focusing optics to irradiate the pre-form along a line parallel to the elongated dimension of the pre-form. The irradiation may result in an increase of the index of refraction of the elongated regions over the index refraction of the remaining regions of the polymer that were not irradiated. After formation of the region of increased index of refraction, the pre-form may be drawn to elongate (and narrow) the pre-form to the desired dimensions of the optical fiber. After elongation, the elongated region of increased index of refraction may function as the core of the optical fiber. The remaining elongated regions of the transparent polymer that were not irradiated may function as cladding of the optical fiber.

In some embodiments of the invention, a fiber of the transparent polymer (e.g., that is already formed with the length and diameter of the fiber) that is coiled into spiral or other curved shape (or otherwise folded or bent) may be irradiated along its length by an appropriately designed optical system to form a core along the length of the fiber. For example, a cylindrical lens of the irradiation optics may be bent into a curved form that is laterally curved substantially identically to the curved fiber. Thus, the curved cylindrical lens my focus irradiation along a curved elongated region that follows the contours of the lens and the fiber.

In some cases, multiple single-core optical fibers that are formed by irradiation of the cladding material, or multicore optical fibers that are formed as described below, may be bundled together and fused to form a single multicore micro-endoscope.

In some embodiments, a multicore micro-endoscope is formed by concurrently irradiating multiple laterally separated elongated regions of a transparent polymer. Thus, each irradiated elongated region may function as a separate fiber optic core, while the regions of the polymer that were not irradiated function as a cladding of the cores. In some cases, the elongated regions may include parallel linear regions laterally separated from one another within the polymer. In other cases, the elongated regions may include similarly shaped and laterally separated (locally parallel) curved regions (e.g., in the form of planar spirals or otherwise).

An optical system for irradiating the transparent polymer may be configured to concurrently irradiate a plurality of elongated regions. Typically, the optical system includes a source of electromagnetic radiation, e.g., an excimer laser or other radiation source that outputs radiation of a wavelength that induces photopolymerization of the transparent polymer.

An arrangement of one or more optical components, e.g., including a cylindrical or otherwise-configured lens or other focusing element, is configured to focus the radiation onto the elongated regions of the transparent polymer. The configuration of the focusing element may be selected in accordance with the shape of the transparent polymer and the intended locations of the irradiated elongated regions. The radiation may thus be focused concurrently onto a plurality of elongated regions within the transparent polymer.

When the elongated regions within the transparent polymer are linear or straight, the plurality of the elongated regions are typically parallel to one another and mutually laterally displaced from one another, e.g., displaced in a dimension that is substantially perpendicular to a longitudinal dimension of the elongated regions. When the elongated regions of the transparent polymer are curved, the curved elongated regions are typically parallel to one another, and mutually laterally displaced from one another (e.g., the displacement in a dimension is substantially perpendicular to an orientation of a local tangent to the curved elongated region).

The optical system may include an arrangement of optical components that enable concurrent focusing of the irradiation to a plurality of elongated regions. These components may include one or more of a plurality of radiation sources (e.g., lasers oriented along different, nonparallel axes), one or more beam-splitting elements (e.g., to split a single beam into multiple beams with different orientations), and one or more beam-shaping elements (e.g., one or more refractive or diffractive elements that cause a lens to focus a beam to multiple focal points, e.g., at different distances from the lens).

In some embodiments, the transparent polymer to be irradiated may be in the form of a pre-form. The pre-form typically is in the form of an elongated block of the transparent polymer. The elongated block may have a circular, rectangular, or otherwise shaped cross section. A long dimension of the pre-form that is parallel to a longitudinal axis of the pre-form is typically much shorter than the length of the multicore micro-endoscope that is to be produced from the pre-form. Similarly, lateral dimensions of the pre-form (e.g., substantially perpendicular to the longitudinal axis) are much larger than the corresponding lateral dimensions of the multicore micro-endoscope.

An optical system for forming multiple optical fiber cores within the pre-form of transparent polymer typically has a cylindrical configuration in which different cross sections of the optical system along a cylindrical axis are substantially identical to one another. The cylindrical axis of the optical system is typically parallel to a longitudinal axis of the pre-form. The optical system is configured to focus radiation that is emitted by the radiation source along multiple focal lines within the pre-form that extend substantially parallelly to the longitudinal axis of the pre-form. Thus, the optical system may induce photopolymerization of the transparent polymer along a plurality of parallel lines within the pre-form. The photopolymerization may increase the index of refraction in a plurality of parallel cylindrical regions of the transparent polymer over the index of refraction of those regions of the transparent polymer that did not undergo photopolymerization.

It may be noted that photopolymerization of the transparent polymer typically reduces the transparency of the transparent polymer. Therefore, irradiation of the transparent polymer along the longitudinal axis of the elongated region (e.g., by a narrow laser beam directed along the longitudinal axis of an elongated pre-form or fiber), may not be practical for producing a uniform core. Accordingly, it is advantageous to induce the photopolymerization by irradiation of the transparent polymer in a lateral direction (e.g., perpendicular to the longitudinal axis of the pre-form or fiber, e.g., using optics with a cylindrical configuration or otherwise) that is perpendicular to the longitudinal axis of the elongated region.

After formation of optical fiber cores by irradiation via the optical system, the pre-form, which remains thermoplastic, may be stretched along the longitudinal axis to form a multicore micro-endoscope. As a result, the diameter or other lateral dimensions of the pre-form are reduced. Similarly, the diameter of each irradiated elongated region of the transparent polymer may be reduced to a diameter that is suitable for an optical fiber for incorporation multicore micro-endoscopy.

In some cases, the radiation source, e.g., a laser, may produce a beam that (e.g., due to its narrowness or nonuniformity) does not uniformly illuminate the cylindrically configured optical system. In such a case, the beam that emerges from the radiation source may be expanded, flattened, or otherwise modified prior to entering the cylindrically symmetric optical system.

In some cases, the cylindrically configured optical system may be configured to irradiate a larger volume of the transparent polymer than that of a single pre-form. In such a case, a plurality of pre-forms may be arranged within the irradiated volume (typically along a single plane that is perpendicular to the optical axis of the cylindrically configured optical system) in order to enable efficient use of the optical system.

In some cases, a pre-form for forming a multicore micro-endoscope may be placed on a stage that is configured move the pre-form in steps relative to the cylindrically configured optical system. In this manner, a system that is configured to focus radiation in one part of the pre-form, e.g., along a single plane or axis, may be utilized to form fiber optic cores throughout the volume of the pre-form.

In accordance with other embodiments, the irradiation may be applied to a full-length fiber (and not a shortened pre-form) in order to cause photopolymerization along the entire length of the fiber. In this case, the fiber may be coiled in a spiral (in a single plane) or otherwise bent to fit within a limited area. In this embodiment, the optical system may not be cylindrically configured. For example, the optical system may be configured to focus the irradiation to multiple points along a single line segment or radius, or along an arc. A stage or other mechanical device may be operated to successively move the fiber to enable focusing the irradiation at successive parts or segments along the length of the fiber.

A system for forming a multicore micro-endoscope, in accordance with some embodiments of the invention, may be advantageous over other prior art techniques for forming a multicore micro-endoscope. For example, a typical prior art method of forming a multicore micro-endoscope could include manufacturing of a pre-form structure made of the cladding material and drilling a bore through the pre-form. The bore could then be filled with a polymer material that is to form the core. The pre-form with the filled bore could then be drawn to elongate the pre-form. Multiple elongated pre-forms could be bundled together and treated thermally to fuse all the pre-forms together. The fused pre-forms could then be further elongated to the desired physical dimensions. With such a prior art process, the drilling would not typically be sufficiently accurate to enable production of an accurately shaped core. Furthermore, since the core and cladding would be made of different polymeric materials, the thermal fusing of the two materials would typically be imperfect. These inaccuracies and imperfections could result in optical transmission losses in the finished multicore fiber.

On the other hand, since, in accordance with some embodiments of the invention, the core is formed by irradiation and photopolymerization of the cladding material, the core and cladding may be effectively bonded. The optical system for irradiating the polymeric material to form the core may be designed to focus the radiation with sufficient accuracy to produce a core of the desired, typically cylindrical, shape.

For example, when irradiating an elongated region of a pre-form, the irradiated region may be sufficiently large such that diffraction spreading of the irradiating beam may be negligible. Therefore, optics with a cylindrical configuration may be designed to accurately focus the irradiation on a linear elongated (e.g., cylindrical) region. After the accurate irradiation of the elongated region to increase the index of refraction of the elongated region, the pre-form may be drawn to elongate the pre-form into an optical fiber in which the non-irradiated regions function as cladding of the irradiated regions which function as cores. Since the irradiated elongated regions were accurately formed, the cores of the resulting optical fibers may also be accurately formed and completely bonded to the cladding. Therefore, the optical losses in a multicore micro-endoscope that is formed in accordance with embodiments of the invention may have lower losses than a multicore micro-endoscope that was formed by prior art techniques.

FIG. 1 schematically illustrates a section of a multicore micro-endoscope, in accordance with some embodiments of the invention.

Multicore micro-endoscope 10 includes a flexible tube 12 that is made of a flexible, plastic, and transparent polymer. The transparent polymer is selected such that irradiation with radiation in a suitable spectral range and of sufficient intensity induces photopolymerization that increases the index of refraction of the irradiated region of the transparent polymer. For example, a suitable transparent polymer may include PMMA or another polymer.

Multicore micro-endoscope includes a plurality of optical fiber cores 14. Each optical fiber core 14 extends along the entire length of multicore micro-endoscope 10 between end faces 16. Each optical fiber core 14 is formed by photopolymerization of an elongated portion of the transparent polymer that forms flexible tube 12. Optical fiber cores 14 are distributed in lateral dimensions (e.g., locally perpendicular to a longitudinal direction represented by longitudinal axis 18) throughout the cross section of flexible tube 12. The non-photopolymerized regions of flexible tube 12 between optical fiber cores 14 function of optical fiber cladding that facilitates minimal losses of light that is transmitted between end faces 16 of multicore micro-endoscope 10.

When multicore micro-endoscope 10 is in use, a proximal, accessible end of multicore micro-endoscope 10 may be connected to one or more of suitable illuminating, magnifying, or viewing optics. A distal end of multicore micro-endoscope 10 may be inserted via an opening into a narrow or otherwise inaccessible region within a body of a living organism, a machine, or other object. Illuminating light may be conducted by optical fiber cores 14 to an otherwise inaccessible surface or object at the distal end of multicore micro-endoscope 10. Light that is reflected or emitted by the surface or object may be transmitted to viewing optics via optical fiber cores 14. Since the arrangement of optical fiber cores 14 is identical at both end faces 16, multicore micro-endoscope 10 may faithfully transmit light that is reflected or emitted by each portion of a viewed surface (e.g., of an organ or object) at a distal end of multicore micro-endoscope 10 to the proximal end. Therefore, the light that exits from optical fiber cores 14 at the proximal end of multicore micro-endoscope 10 may faithfully represent the viewed surface.

Figure 2:
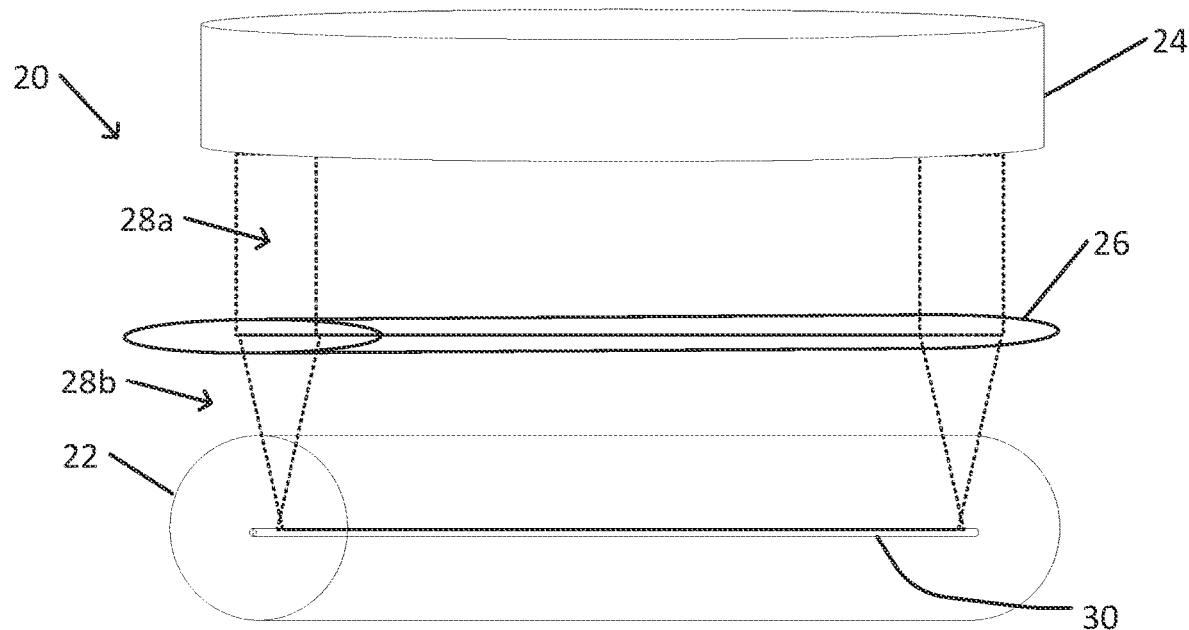
FIG. 2 schematically illustrates a system to irradiate a transparent polymer to form a single core of the multicore micro-endoscope shown in FIG. 1.

FIG. 2 schematically illustrates a system to irradiate a transparent polymer to form a single core of the multicore micro-endoscope shown in FIG. 1.

Core formation system 20 is configured to induce photopolymerization of a single elongated region of transparent polymer 22. For example, transparent polymer 22 may represent a pre-form or a fiber that is composed of a suitable flexible transparent polymer whose index of refraction is increasable by photopolymerization. For example, transparent polymer 22 may include PMMA or another suitable polymer. The cross section of transparent polymer 22 may be round, as in the example shown, may be rectangular, or may have another form.

Radiation source 24 is configured to produce a beam of electromagnetic radiation within a spectral range that induces photopolymerization in transparent polymer 22. For example, if photopolymerization requires radiation in the ultraviolet spectral range, radiation source 24 may include an excimer laser.

In some cases, radiation source 24 may include beam-expander optics for increasing a diameter of emitted beam 28a of the emitted radiation to a size that is sufficient to concurrently irradiate the entire length of a pre-form of transparent polymer 22. In other cases, e.g., where a fiber of transparent polymer 22 is to be irradiated, the diameter of emitted beam 28a may be sufficient to irradiate a section of the fiber of predetermined length.

In some cases, in addition to or in place of beam-expander optics, radiation source 24 may include optical elements that are configured to increase the homogeneity of emitted beam 28a within a given cross section of emitted beam 28a.

Cylindrical lens 26 is configured to focus emitted beam 28a as focused beam 28b along elongated region 30 of transparent polymer 22. Cylindrical lens 26 may include a simple lens or a compound lens. Alternatively, or in addition to cylindrical lens 26, focusing optics of core formation system 20 may include one or more reflective (e.g., one or more cylindrical mirrors) or diffractive optical components.

The intensity of focused beam 28b at elongated region 30 may be sufficient to induce photopolymerization in elongated region 30 while the remainder of transparent polymer 22 does not undergo photopolymerization. Thus, irradiation by focused beam 28b may increase the index of refraction within elongated region 30 over the index of refraction of the remainder of transparent polymer 22.

When transparent polymer 22 is in the form of a pre-form and after irradiation of elongated region 30, transparent polymer 22 may be stretched along its elongated dimension, e.g., parallel to elongated region 30, to form an optical fiber of suitable diameter. Typically, after elongation, the stretched transparent polymer 22 may be cut into separate fibers of suitable length for construction of multicore micro-endoscope 10. For example, a suitable length may be approximately one meter for a multicore micro-endoscope 10 that is suitable for examining some parts of the interior of a human body. Other lengths may be suitable for other applications.

In one example, a pre-form of transparent polymer 22 may have a length of about 10 cm and a diameter of about 1 cm. After irradiation by core formation system 20, the pre-form may be stretched to form an optical fiber with a diameter of about 0.5 mm. In order to achieve the desired fiber diameter in this example, the original 10 cm length of the pre-form must be stretched to a length of about 40 m. Thus, the irradiation of elongated region 30 the pre-form may enable production of about 40 optical fibers that are each one meter long.

In some cases (e.g., where an optical system has not been configured to concurrently irradiate all form all of the elongated regions 30 that are required to form all of the optical fiber cores 14 required for a particular multicore micro-endoscope 10), a plurality of fibers that are formed by core formation system 20 may be bundled together and fused (e.g., by heating) to form a single multicore micro-endoscope 10.

If transparent polymer 22 is in the form of a fiber, core formation system 20 may additionally include a mechanism for sequentially irradiating successive segments of transparent polymer 22. For example, core formation system 20 may additionally include a spooling mechanism for advancing transparent polymer 22 after irradiation one segment of elongated region 30, to enable irradiation of an adjacent segment of elongated region 30. After irradiation of the entire length of transparent polymer 22 in the form of a fiber, the fiber may be cut to length, bundled together, and fused, to form a single multicore micro-endoscope 10.

In accordance with some embodiments of the invention, a system may be configured to concurrently irradiate parallel elongate regions of a transparent polymer.

Figure 3:
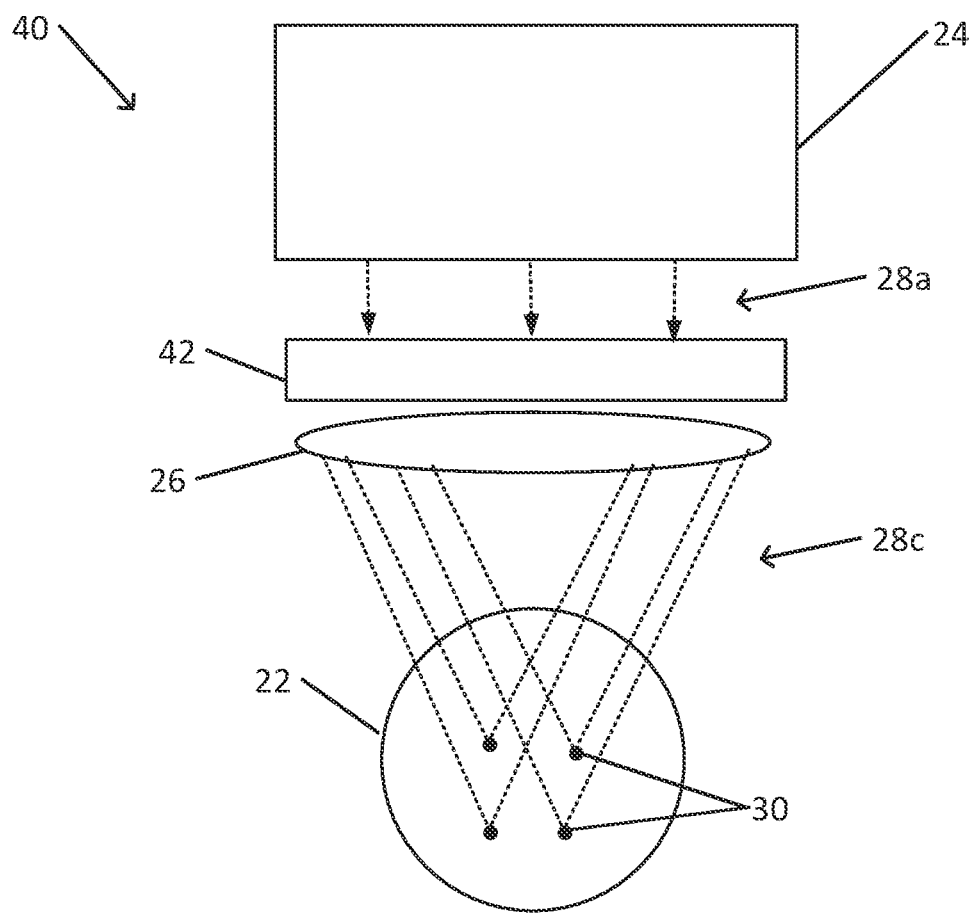
FIG. 3 schematically illustrates a cross-sectional view of a system to irradiate a transparent polymer to concurrently form multiple cores of the multicore micro-endoscope shown in FIG. 1.

FIG. 3 schematically illustrates a cross-sectional view of a system to irradiate a transparent polymer to concurrently form multiple cores of the multicore micro-endoscope shown in FIG. 1.

In the example shown, multicore formation system 40 is shown as a cross-sectional view of a system with a cylindrical configuration (e.g., similar to core formation system 20 as shown in FIG. 2). Multicore formation system 40 is configured to concurrently irradiate a plurality of elongated regions 30 within transparent polymer 22.

In some cases, transparent polymer 22 may be in the form of one or more pre-forms. For example, where multicore formation system 40 is configured to irradiate an area that is sufficiently large to cover a plurality of pre-forms of transparent polymer 22 (e.g., when placed laterally adjacent to one another), multicore micro-endoscope 10 may include structure (e.g., a holder or platform) that enables placement of the plurality pre-forms in the optical field of multicore formation system 40.

Multicore formation system 40 includes one or more radiation sources 24 (e.g., excimer lasers or other sources) that are each configured to produce a beam of electromagnetic radiation within a spectral range (e.g., ultraviolet or another spectral range) that may induce photopolymerization in transparent polymer 22 (e.g., PMMA or another polymer). For example, two or more radiation sources 24 may be oriented to emit emitted beams 28a at different angles (e.g., within the lateral plane of the cross section of FIG. 3). Alternatively or in addition, radiation source 24 may include beam-splitting components that split a single emitted beam 28a into a plurality of beams with different orientations.

In some cases, radiation source 24 may include beam-expander optics, optical elements to increase the homogeneity of emitted beam 28a, or both.

Multicore formation system 40 includes multifocal optics 42 that enables cylindrical lens 26 (or any other or additional reflective or diffractive focusing elements) to focus emitted beam 28a to a plurality of elongated regions 30 within transparent polymer 22. For example, multifocal optics 42 may include beam-splitting components as described above.

Multifocal optics 42 may include one or more diffractive or refractive beam-shaping elements that enable cylindrical lens 26 to focus radiation to a plurality of elongated regions 30 (e.g., parallel focal lines, in the cylindrical configuration of multicore formation system 40) within transparent polymer 22.

Thus, when a pre-form of transparent polymer 22 with multiple irradiated and photopolymerized elongated regions 30 is stretched to form an optical fiber, the resulting optical fiber may include a plurality of laterally separated fiber optic cores. As discussed above, a plurality of such multicore optical fibers may be bundled and fused together to form multicore micro-endoscope 10.

In some cases, a system similar to multicore formation system 40 may be configured to irradiate a fiber transparent polymer 22.

Figure 4:
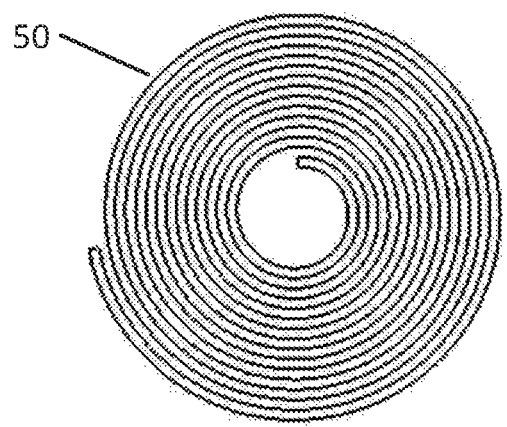
FIG. 4 schematically illustrates an example of a configuration of a fiber of transparent polymer for irradiation by the system shown in FIG. 3.

FIG. 4 schematically illustrates an example of a configuration of a fiber of transparent polymer for irradiation by the system shown in FIG. 3.

In the example shown, polymer fiber 50 has been wound into a spiral coil configuration.

In one example of irradiation of polymer fiber 50 in the configuration shown, a system such as multicore formation system 40 may be modified such that the configuration is no longer linearly cylindrical.

For example, a curved cylindrical lens may be laterally curved in a plane that is perpendicular to the optic axis (plane) of the cylindrical lens. In the example shown, a curved cylindrical lens may be shaped similarly to the spiral form of polymer fiber 50. Thus, the curved cylindrical lens may focus the irradiation (e.g., after having been modified by suitably configured multifocal optics 42) to a plurality of curved elongated regions, where each curved elongated region extends along the entire length of polymer fiber 50.

In another example, e.g., where the irradiation optics are limited to a relatively simple configuration, a multicore formation system may be designed to concurrently irradiate a plurality of arcs of different radius. Polymer fiber 50 may be mounted on a stage that is configured to rotate and laterally translate a surface that is configured to support polymer fiber 50. The stage may be operated to sequentially irradiate different sectors of polymer fiber 50.

Figure 5:
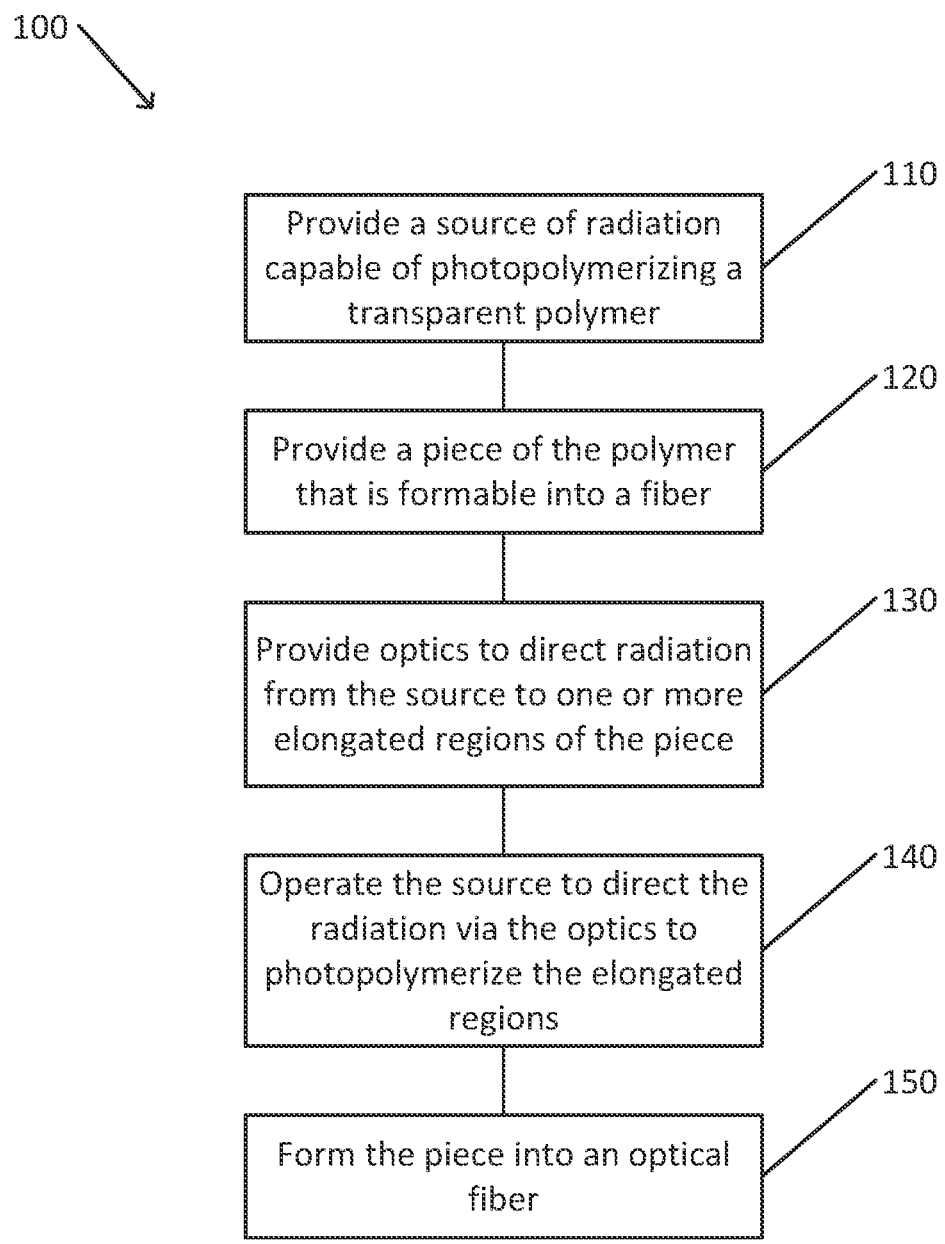
FIG. 5 is a flowchart depicting a method for producing a multicore micro-endoscope, in accordance with an embodiment of the present invention.

FIG. 5 is a flowchart depicting a method for producing a multicore micro-endoscope, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Multicore micro-endoscope production method 100 may be executed by a user or computerized controller of a system for producing a multicore micro-endoscope 10. Such a system may include core formation system 20, multicore formation system 40, or another system.

A source of radiation is provided (block 110), e.g., one or more radiation sources 24, that produces electromagnetic radiation in a spectral range (e.g., ultraviolet radiation) and with sufficient intensity to photopolymerize a selected transparent polymer 22 (e.g., PMMA or another polymer).

A suitably sized piece of the selected transparent polymer is provided (block 120), e.g., by placement in or on a suitably sized and positioned holding structure. The piece may be provided in the form of a pre-form that may be stretched and cut to form optical fibers of desired dimensions, or may be in the form of an optical fiber.

One or more optical components are provided to focus or otherwise direct radiation that is emitted by the source to the piece of transparent polymer (block 130). The optical components may include a combination of one or more of cylindrical or other lenses or mirrors, refractive or diffractive beam-shaping elements, beam splitting or directing elements, or other optical components. In addition, mechanical positioning components may be provided to manipulate the piece of transparent polymer relative to the radiation source and the optical components.

The radiation source may then be operated such that radiation that is emitted by the radiation source is directed by the optical components (and, where appropriate, by mechanical components) to one or more elongated regions of the transparent polymer (block 140). The directed radiation may then induce photopolymerization of the elongated regions to increase the index of refraction of the elongated regions. Regions of the transparent polymer that laterally surround each of the elongated regions do not undergo photopolymerization, such that the index of refraction of the non-photopolymerized regions remains lower than the index of refraction of the photopolymerized elongated regions.

For example, optical components in a cylindrical configuration may direct the radiation to the elongated regions. In another example, a mechanical stage may sequentially bring successive adjacent regions of the transparent polymer to a position where the emitted radiation is directed to each successive adjacent region.

After irradiation, the piece of the transparent polymer may be formed into one or more optical fibers, with the irradiated elongated regions functioning as optical fiber cores (block 150). For example, when the piece of the transparent polymer is a pre-form, the pre-form may be stretched until its dimensions (e.g., a diameter or other lateral dimension) are those of desired optical fiber. The fiber that is formed by the stretching may be cut to a length that is suitable for a particular application. Similarly, if the piece of transparent polymer is in the form of a fiber, the fiber may be cut to the suitable length.

A plurality of such optical fibers may be bundled and fused together to form a component of a multicore micro-endoscope.

Different embodiments are disclosed herein. Features of certain embodiments may be combined with features of other embodiments; thus, certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for producing a multicore optical fiber, the method comprising:
    providing a transparent polymer whose index of refraction is increasable by irradiation that induces photopolymerization of the transparent polymer;
    providing a source of radiation that is capable of inducing photopolymerization in the transparent polymer; and
    directing the radiation by one or more optical components to a plurality of elongated regions within the transparent polymer to induce the photopolymerization of the transparent polymer within the plurality of elongated regions, each of the elongated regions surrounded by a region of the transparent polymer that was not photopolymerized, such that in an optical fiber that is formed of the transparent polymer after the photopolymerization, each of the elongated regions functions as a core of the optical fiber and the region that surrounds each of the elongated regions functions as a cladding of each of the cores.

2. The method of claim 1, wherein the transparent polymer is provided in the form of a pre-form of the transparent polymer.

3. The method of claim 2, further comprising stretching the pre-form to dimensions of the optical fiber.

4. The method of claim 1, wherein the one or more optical components comprise a beam-shaping component to enable concurrent irradiation of a plurality of the cores.

5. The method of claim 1, wherein the transparent polymer is provided in the form of a fiber of the transparent polymer.

6. The method of claim 5, wherein the fiber of the transparent polymer is provided in the form of a spiral coil.

7. The method of claim 5, wherein directing the radiation comprises successively directing the radiation to the plurality of the elongated regions in one part of the fiber of the transparent polymer, and mechanically moving the fiber of the transparent polymer, and directing the radiation to the plurality of the elongated regions in another part of the fiber of the transparent polymer.

* * * * *